(12) United States Patent
Ding

(10) Patent No.: US 6,650,930 B2
(45) Date of Patent: Nov. 18, 2003

(54) COMPUTER ASSISTED RADIOTHERAPY DOSIMETER SYSTEM AND A METHOD THEREFOR

(75) Inventor: Wei Ding, Kanata (CA)

(73) Assignee: Thomson & Nielsen Electronics Ltd., Nepean (CA)

( * ) Notice: Subject to any disclaimer, the term of this patent is extended or adjusted under 35 U.S.C. 154(b) by 0 days.

(21) Appl. No.: 09/978,595

(22) Filed: Oct. 18, 2001

(65) Prior Publication Data

US 2002/0049362 A1 Apr. 25, 2002

(30) Foreign Application Priority Data

Oct. 20, 2000 (CA) .............................................. 2324048

(51) Int. Cl.$^7$ ................................................. A61B 6/00
(52) U.S. Cl. ........................................ 600/436; 128/920
(58) Field of Search ................................. 600/425, 426, 600/436, 1–3; 128/899, 920

(56) References Cited

U.S. PATENT DOCUMENTS

| 5,621,779 | A | | 4/1997 | Hughes et al. |
|---|---|---|---|---|
| 5,923,724 | A | | 7/1999 | Soukal |
| 6,266,453 | B1 | * | 7/2001 | Hibbard et al. ............. 382/294 |
| 6,398,710 | B1 | * | 6/2002 | Ishikawa et al. ............... 600/3 |
| 6,405,072 | B1 | * | 6/2002 | Cosman ..................... 600/426 |

FOREIGN PATENT DOCUMENTS

GB          1362679          8/1974

* cited by examiner

*Primary Examiner*—Shawna J Shaw
(74) *Attorney, Agent, or Firm*—Thomas Adams

(57) ABSTRACT

In order to facilitate the display and evaluation of data acquired while irradiating a body, e.g. a patient undergoing radiation therapy, a dosimetry system has a plurality of sensors for disposition on, in or near the body to be irradiated and connected to a sensor reading instrument which is interfaced with a display system, for example a personal computer, which is arranged to display, in use, one or more representations, for example drawings or photographs, of the body to be irradiated, along with the positions and the dose data for those specific locations where the dosimeter sensors were placed.

21 Claims, 17 Drawing Sheets

FIG. 2

Step 1: Pre-Irradiation

Current Action: Check Dosimeters

Reader's Messages
- ○ Show All   ○ Hide
- ● Show Recent

SETUP:
UNIT:
LOCATION:
ENERGY:
SSD:
GANTRY ANGLE:
COLLIMATION:
FIELD SIZE:
EXPOSURE:

08:50:55 2000-10-02
ZERO DOSIMETERS

B1 TOTAL: 12,638 mV
B2 TOTAL: 17,417 mV
B3 TOTAL: 17,221 mV
B4 TOTAL: 113 mV
B5

Calibrating Parameters / Print

| Dosimeter | CF | CR |
|---|---|---|
| A1 | 01.00 mVcGy | 1.000 |
| A2 | 01.00 mVcGy | 1.000 |
| A3 | 01.00 mVcGy | 1.000 |
| A4 | 01.00 mVcGy | 1.000 |
| A5 | 01.00 mVcGy | 1.000 |
| B1 | 01.00 mVcGy | 1.000 |
| B2 | 01.00 mVcGy | 1.000 |
| B3 | 01.00 mVcGy | 1.000 |
| B4 | 01.00 mVcGy | 1.000 |
| B5 | 01.00 mVcGy | 1.000 |
| C1 | 01.00 mVcGy | 1.000 |
| C2 | 01.00 mVcGy | 1.000 |
| C3 | 01.00 mVcGy | 1.000 |
| C4 | 01.00 mVcGy | 1.000 |
| C5 | 01.00 mVcGy | 1.000 |
| D1 | 01.00 mVcGy | 1.000 |
| D2 | 01.00 mVcGy | 1.000 |
| D3 | 01.00 mVcGy | 1.000 |
| D4 | 01.00 mVcGy | 1.000 |
| D5 | 01.00 mVcGy | 1.000 |

Dosimeter Checking Records / Clear

| Time | Total Voltage | Notes |
|---|---|---|
| | | |
| | | |
| | | |
| | | |
| | | |
| 08:50:55 | TOTAL: 12,638 mV | |
| 08:50:55 | TOTAL: 17,417 mV | |
| 08:50:55 | TOTAL: 17,221 mV | |
| 08:50:55 | TOTAL: 113 mV | |
| | | |

To check dosimeters, connect the corresponding Bias Supply to the Reader, and press the Reader's START button (or ZERO button) for 1 second.

[2000-10-02]   [Cancel] [Finish]   [Next Step] [Exit]

FIG. 6B

Step 2: Treatment Info.

Treatment Information for Patient #1 | Show Picture

Patient Count = 4
Current Patient: #1
*John Smith*

☑ ⦿ Patient #1
☐ ○ Patient #2
☐ ○ Patient #3
☐ ○ Patient #4

< Patient Information >

- First Name: John
- Last Name: Smith
- Registry #: 12345678
- Gender (M/F): M

Import Existing Treatment Info

< Treatment Plan Ref. >

- Fraction: 1
- Wedges: None
- Block: None

< Radiation Settings >

- Energy: 18 MV
- SSD: 90 cm
- Gantry Angle: 0 deg.
- Collimation: N/A
- Field Size: 10 x10
- MU: 100

Radiation Machine

- Type: Linac
- S/N: 456

TN-RD-50 Reader

- S/N: 278

Dosimeter - Assigning Table

| Dosimeter | Patient | Site of Dosimeter | Target Dose |
|---|---|---|---|
| A1 | | | |
| A2 | | | |
| A3 | | | |
| A4 | | | |
| A5 | | | |
| B1 | #1 | Site 1 | 100 cGy |
| B2 | #1 | Site 2 | 100 cGy |
| B3 | #1 | Site 3 | 100 cGy |
| B4 | #1 | Site 4 | 100 cGy |
| B5 | #1 | Site 5 | 100 cGy |
| C1 | | | |
| C2 | | | |
| C3 | | | |
| C4 | | | |
| C5 | | | |
| D1 | | | |
| D2 | | | |
| D3 | | | |
| D4 | | | |
| D5 | | | |

Please fill in the treatment information for the current patient.
To assign (or cancel) dosimeters, click on the 'Dosimeter' column.
To indicate the sites of dosimeters graphically, click on 'Show Picture'.

2000-10-02

[Back to Step 1] [Apply] [Cancel]

[Exit]

Step 3: Measuring Dose

TN - DOSE REPORTER V2.31

Reader's Messages
- ● Show All  ○ Hide
- ○ Show Recent

```
09:01:49 2000-10-02
B3 DOSE: 100 cGy
B3 TOTAL: 17,212 mV

09:01:51 2000-10-02
B4 DOSE: 100 cGy
B4 TOTAL: 113 mV

09:01:53 2000-10-02
B5 DOSE:
B5 TOTAL:
```

Records of Measurement — Clear

| Dosimeter | Patient & Site | Time | Voltage | Dose | Target | Deviation |
|---|---|---|---|---|---|---|
| A1 | | | | | | |
| A2 | | | | | | |
| A3 | | | | | | |
| A4 | | | | | | |
| A5 | | | | | | |
| B1 | #1, Site 1 | 09:01:42 | N/A | 100 cGy | 100 cGy | 0 % |
| B2 | #1, Site 2 | 09:01:47 | N/A | 105 cGy | 100 cGy | 5 % |
| B3 | #1, Site 3 | 09:01:49 | N/A | 100 cGy | 100 cGy | 0 % |
| B4 | #1, Site 4 | 09:01:51 | N/A | 100 cGy | 100 cGy | 0 % |
| B5 | #1, Site 5 | 09:01:53 | N/A | 102 cGy | 100 cGy | 2 % |
| C1 | | | | | | |
| C2 | | | | | | |
| C3 | | | | | | |
| C4 | | | | | | |
| C5 | | | | | | |
| D1 | | | | | | |
| D2 | | | | | | |
| D3 | | | | | | |
| D4 | | | | | | |
| D5 | | | | | | |

Recording is ongoing. Connect Reader to BIAS SUPPLY(S), then press its 'READ' button(s).
Click on 'Stop' when measurement finished.

[Back to Step] [Record] [Stop]

2000-10-02                                                    [Exit]

FIG. 6E

CHECKED WHEN INPUTTING IS FINISHED

PATIENT SELECTION

☐ TN - DOSE REPORTER V2.31

Step 2: Treatment Info.

Patient Count = 4
Current Patient: #1
*John Smith*

☑ ⦿ Patient #1
☑ ○ Patient #2
☑ ○ Patient #3
☑ ○ Patient #4

Treatment Information for Patient #1 | Show Picture

< Patient Information >
- First Name: John
- Last Name: Smith
- Registry #: 12345678
- Gender (M/F): M < Radiation Settings >
- Energy: 18 MV
- SSD: 90 cm
- Gantry Angle: 0 deg.
- Collimation: N/A
- Field Size: 10 x 10
- MU: 100

Radiation Machine
- Type: Linac
- S/N: 456

TN-RD-50 Reader
- S/N: 278

Import Existing Treatment Info

< Treatment Plan Ref. >
- Fraction: 1
- Wedges: None
- Block: None

Dosimeter - Assigning Table

| Dosimeter | Patient | Site of Dosimeter | Target Dose |
|---|---|---|---|
| A1 | | | |
| A2 | | | |
| A3 | | | |
| A4 | | | |
| A5 | | | |
| B1 | #1 | Site 1 | 100 cGy |
| B2 | #1 | Site 2 | 100 cGy |
| B3 | #1 | Site 3 | 100 cGy |
| B4 | #1 | Site 4 | 100 cGy |
| B5 | #1 | Site 5 | 100 cGy |
| C1 | | | |
| C2 | | | |
| C3 | | | |
| C4 | | | |
| C5 | | | |
| D1 | | | |
| D2 | | | |
| D3 | | | |
| D4 | | | |
| D5 | | | |

Please fill in the treatment information for the current patient.
To assign (or cancel) dosimeters, click on the 'Dosimeter' column.
To indicate the sites of dosimeters graphically, click on 'Show Picture'.

Back to Step 1 | Apply | Cancel 2000-10-02 | Exit

☐ TN - DOSE REPORTER V2.31

Step 3: Measuring Dose

Reader's Messages
○ Show All   ● Show Recent

```
09:01:50 2000-10-02

B3 DOSE: 100 cGy
B3 TOTAL: 17,212 mV

09:01:51 2000-10-02

B4 DOSE: 100 cGy
B4 TOTAL: 113 mV

09:01:53 2000-10-02

B5 DOSE:
B5 TOTAL:
```

Records of Measurement                                        Clear

| Dosimeter | Patient & Site | Time | Voltage | Dose | Target | Deviation |
|---|---|---|---|---|---|---|
| A1 | | | | | | |
| A2 | | | | | | |
| A3 | | | | | | |
| A4 | | | | | | |
| A5 | | | | | | |
| B1 | #1, Site 1 | 09:01:42 | N/A | 100 cGy | 100 cGy | 0 % |
| B2 | #1, Site 2 | 09:01:47 | N/A | 105 cGy | 100 cGy | 5 % |
| B3 | #1, Site 3 | 09:01:49 | N/A | 100 cGy | 100 cGy | 0 % |
| B4 | #1, Site 4 | 09:01:51 | N/A | 100 cGy | 100 cGy | 2 % |
| B5 | #1, Site 5 | 09:01:53 | N/A | 102 cGy | 100 cGy | |
| C1 | | | | | | |
| C2 | | | | | | |
| C3 | | | | | | |
| C4 | | | | | | |
| C5 | | | | | | |
| D1 | | | | | | |
| D2 | | | | | | |
| D3 | | | | | | |
| D4 | | | | | | |
| D5 | | | | | | |

[Back to Step]  [Record]  [Stop]

Recording is ongoing. Connect Reader to BIAS SUPPLY(s), then press its READ button(s).
Press 'Stop' when measurement finished.

2000-10-02                                              [Exit]

Step 4: Viewing/Printing Reports

The Current Report is of Patient #1

● Patient #1
○ Patient #2
○ Patient #3
○ Patient #4
○ others

Report Summary

Patient Name : John Smith
Registry # : 123456789
Gender : M
Image : #0
Finish Time : 09:02 / Oct 02 2000

| Dosimeter B1 : | Site @ Site 1 | Dose = 100 cGy |
| | Target Dose = 100 cGy | Deviation = 0 % |
| Dosimeter B2 : | Site @ Site 2 | Dose = 105 cGy |
| | Target Dose = 100 cGy | Deviation = 5 % |
| Dosimeter B3 : | Site @ Site 3 | Dose = 100 cGy |
| | Target Dose = 100 cGy | Deviation = 0 % |
| Dosimeter B4 : | Site @ Site 4 | Dose = 100 cGy |
| | Target Dose = 100 cGy | Deviation = 0 % |
| Dosimeter B5 : | Site @ Site 5 | Dose = 102 cGy |
| | Target Dose = 100 cGy | Deviation = 2 % |

Click Here To Start A New Measurement

< Back    Print    Save    Open

Comments: Doses within target tolerances.

2000-10-02

Exit

FIG. 7F

COMPUTER ASSISTED RADIOTHERAPY DOSIMETER SYSTEM AND A METHOD THEREFOR

TECHNICAL FIELD

The invention relates to radiotherapy dosimeter systems, especially of the kind which use a plurality of dosimeter sensors distributed in a region to be irradiated and means for monitoring radiation levels detected by the sensors.

BACKGROUND ART

Radiotherapy treatment of cancer patients involves the use of machines which produce high energy X-rays or high energy electrons. It is common practice to verify the radiation dose delivered to the patient with a dosimetry system such as the Thomson & Nielsen Patient Dose Verification System.

There are three different types of dosimetry system used in radiotherapy. These are based on (a) film or thermal luminescent dosimeters (TLD), (b) diodes and (c) MOSFETs. Diode and MOSFET systems use electronic dosimeter sensors together with electronic reading systems, whereas film or TLD use chemical or thermal methods of reading the detectors into an electronic reading system.

Since diode and MOSFET based dosimetry systems have the convenience of direct electronic reading of the dosimeters, they also have the potential advantage of direct data communication with computer systems. The person using a patient dosimetry system (usually a medical physicist, dosimetrist or therapist) requires the radiation dose information from the system to be in a format that is suitable for good quality assurance records.

The state of the art with patient dose verification systems is for the dose data to be presented in one of three formats— (a) on a display on the reading instrument, (b) on a print-out from the electronic reader or (c) on a computer screen. In the latter case, the information presented on the computer screen is in the form of numbers and, in some cases, graphs.

Thomson & Nielsen MOSFET dosimetry systems use Excel™ spreadsheets for this purpose. Sun Nuclear™ and Scanditronix™ have diode-based systems which use Windows™—based systems with numerical tables and graphs of data.

A disadvantage of these known systems is that it is not easy to confirm that the dose values measured were taken at the proper locations on the body of the patient.

SUMMARY OF INVENTION

An object of the present invention is to at least mitigate this disadvantage and to this end, there is provided a dosimetry system having means for displaying a representation of the body, e,g., a patient, to be irradiated, showing specific locations of radiation sensors in relation to the body.

According to one aspect of the present invention, there is provided a dosimetry system comprising display means; display control means for controlling the display means to provide, simultaneously, a display image comprising a representation of at least a portion of a body to be irradiated and a plurality of graphics artefacts each comprising a sensor icon representing a respective one of a plurality of radiation sensors to be positioned in, on or adjacent said body during subsequent irradiation of the body, and a corresponding identifier; user-operable means for controlling the display control means to relocate, selectively, some or all of the sensor icons at respective positions on or adjacent said body image, said positions corresponding to positions on, in or adjacent said body at which the sensors themselves are to be positioned during subsequent irradiation of the body, and outputting to one or both of storage means and recording means a record of the displayed image showing the body image and graphics artefacts with the sensor portions positioned as relocated.

Preferably, the display system is arranged to display the representations, prior to irradiation, with the sensor location artefacts and sensor identifiers and, after irradiation, with the measured doses associated with each sensor.

Preferably, the display system provides for adjustment of the sensor location artefacts prior to the irradiation, to select desired locations, and then may provide for printing of the representations, showing the sensor location artefacts, prior to irradiation, thus allowing the print-out to be used by an operator as a guide when positioning the sensors.

A method of determining locations of radiation sensors in, on or adjacent a body during subsequent irradiation thereof by a radiation therapy system, comprising the steps of:

(I) displaying on a display device, simultaneously, a representation of at least a portion of the body to be irradiated, and a plurality of graphics artefacts each representing a respective one of a plurality of radiation sensors to be positioned in, on or adjacent said body during subsequent irradiation of the body, each graphics artefact comprising a sensor icon and a sensor identifier;

(ii) controlling the display means to relocate, selectively, some or all of the sensor icons of the graphics arrefacts at respective positions on or adjacent said representation, said positions corresponding to positions on, in or adjacent said body at which the radiation sensors represented by the selected sensor icons are to be positioned during subsequent irradiation of the body, and (iii) outputting to one or both of storage means and recording means a record of the displayed representation and graphics anefacts with the sensor icons in their relocated positions.

Embodiments of the invention advantageously enable the physicist to plan the locations where dose measurements are required, ensure that the dosimeters are placed according to plan, and confirm that the body (patient) has received the correct dose to the correct location according to the plan.

Yet another advantageous feature is that the one or more representations of the body, together with the preselected dosimeter sensor locations, may be printed prior to patient treatment so as to facilitate correct positioning of the dosimeter sensors in the correct anatomical positions by the medical personnel performing the radiotherapy procedure.

Advantageously, embodiments of the present invention may provide real-time display of data from the dosimetry system reader.

Another advantageous feature is that the patent's treatment information may be readily recorded (e.g. patient's name, identification of radiotherapy machine used, energy of the machine).

The one or more representations used to indicate the positions of the dosimeter sensors on the body, e.g. on the patient's anatomy, may comprise standard line drawings or custom images, such as scanned photographs or digital camera images. In the latter cases, the use of actual images of the body facilitates proper location of the sensors.

Another advantageous feature of embodiments of the present invention which use a computer display is that the software may calculate the radiation dose using the data input from the reading instrument and any calibration or correction factors previously input by the physicist, typically following a previous calibration of the dosimetry system in a known manner. The software then may compare the dose calculations with predetermined target doses and indicate, conveniently by highlighting in the display, any deviation for corrective action.

A further feature of embodiments of the present invention is the capability to view, print or electronically save the final report with all the relevant dosimetry data collected during the patient's treatment.

According to a third aspect of the invention there is provided software for interfacing a plurality of dosimeter sensors and a reader to a microcomputer or personal computer to provide for the display of an image or other representation of the body/patient and the locations of the sensors in relation to the body, in a system according to the first aspect.

BRIEF DESCRIPTION OF THE DRAWINGS

A dosimetry system in accordance with the invention will now be described, by way of example, with reference to the accompanying drawings, in which:

FIG. 2 illustrates a portion of a display of the system;

FIGS. 6A to 6F and FIGS. 7A to 7F show display screens displayed during operation of the system.

DETAILED DESCRIPTION OF A PREFERRED EMBODIMENT

Figure 1:
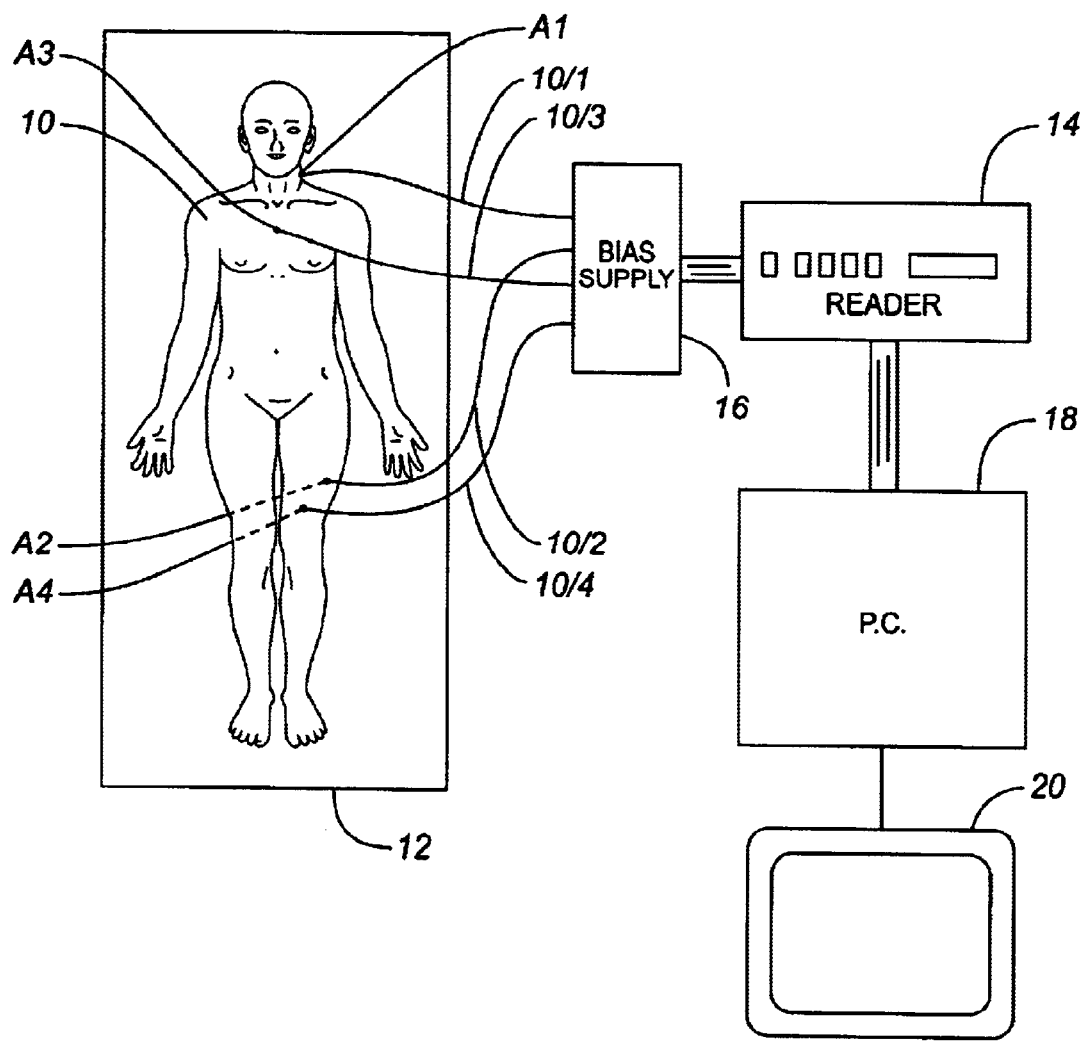
FIG. 1 illustrates, partially and schematically, a dosimetry system for irradiating a person.

A dosimetry system for monitoring the amount of radiation to which a patient is subjected will be described with reference to FIG. 1 which illustrates a patient 10 who is to receive radiation therapy while lying on a table 12. The therapy entails irradiating the patient 10 by means of a radiation therapy machine, which might be an X-ray machine, a CT scanner, or other machine having means (not shown) for irradiating the patient. The dosimetry system comprises a set of MOSFET radiation sensors A1 . . . A4 positioned at predetermined locations on the patient's body and connected by leads 10/1 . . . 10/4, respectively, to a reader 14 (e.g. Thomson & Neilsen's reader, Model No. 50 [TN-RD-50]) by way of a bias supply unit 16. The reader 14 is connected to a personal computer 18 which controls a display device 20. The sensors A1–A4, bias supply 16, reader 14 and computer 18 may be of known construction and so will not be described in detail. The personal computer 18 is equipped with the system software, such as Visual Basic™, or the like, suitably configured, as will be described hereafter. The sensors A1–A4 and, when applicable, other parts of the dosimetry system, have been previously calibrated using known techniques.

Operation of the dosimetry system involves two main phases, namely (i) assignment of graphics artefacts representing the sensors to selected positions on the representations, and (ii) measurement and display of the measured doses. These two phases need not be performed at the same time. For the first phase, the patient need not be present and, in fact, the first phase could be carried out remotely from the radiation therapy machine. For convenience, however, both phases will be described as if carried out together.

Figure 2:
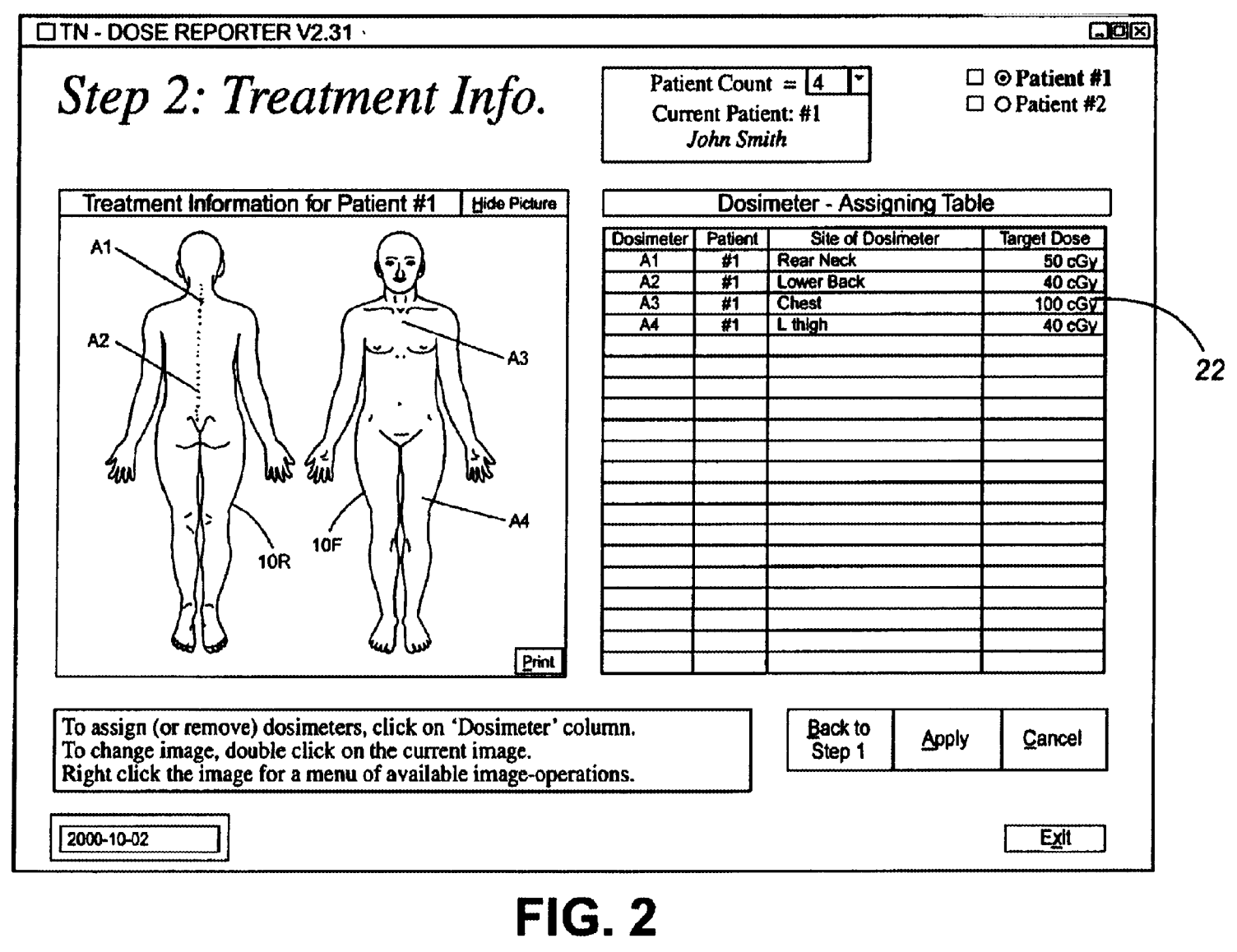

FIG. 2 illustrates a portion of the display 20 controlled by the computer 18 and showing representations of the patient 10; specifically, in outline, front 10F and rear 10R line drawings representing the patient 10 and positions of graphics artefacts representing the four dosimeter sensors A1, A2, A3, and A4. The display also shows a table 22 listing the sensors A1–A4 and associated data. When the irradiation process has been carried out, the data will include the dose measured by each sensor.

Figure 3A:
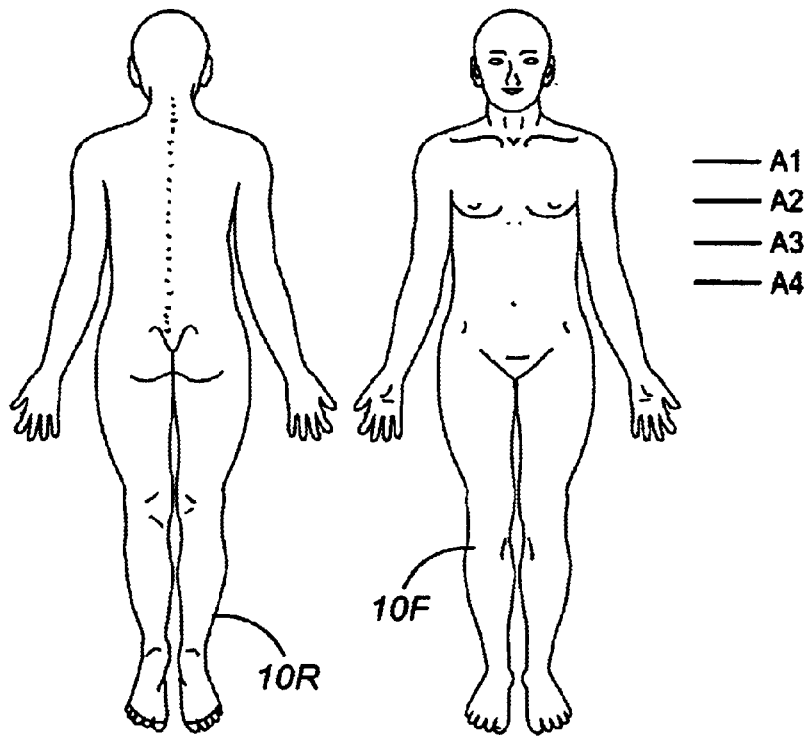
FIG. 3A illustrates a representation displayed during assignment of sensor positions.

FIG. 3A illustrates the type of graphic representation first shown to the user on the computer screen 20, when the sensor artefacts have not been assigned, but merely grouped to the right of the image 10F. The sensors A1, A2, A3 and A4 are represented by graphics artefacts comprising respective sensor icons, specifically dots connected by lead lines to respective labels (sensor identifiers) A1–A4.

Figure 3B:
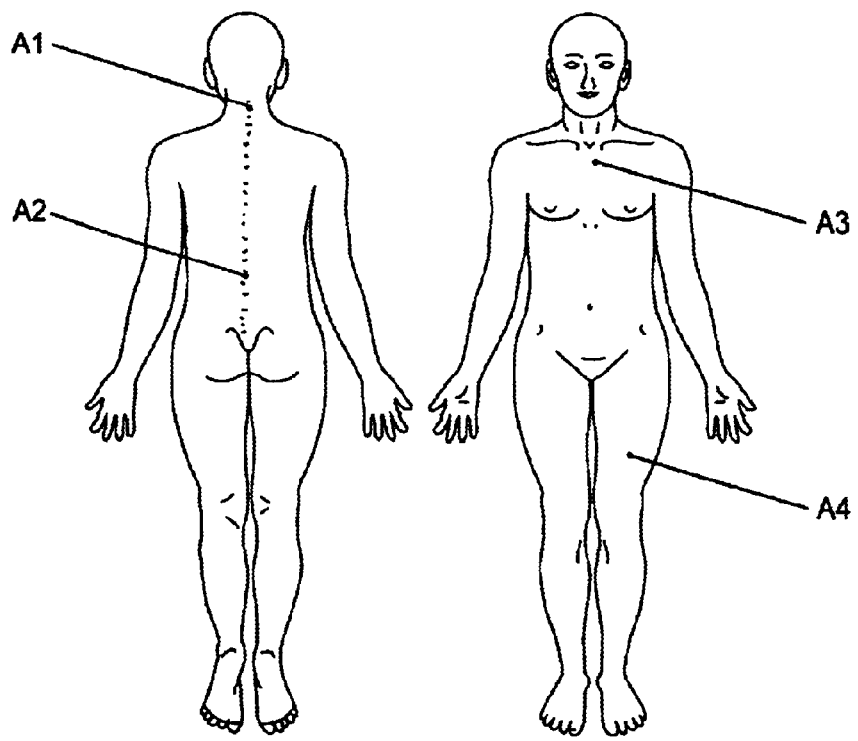
FIG. 3B illustrates a representation subsequently displayed during assignment of sensor positions.

Initially, the computer prompts the user to assign dosimeter sensors to various parts of the anatomy, which the user does by "dragging and dropping" the dots and identifiers. Once this task has been completed, the display screen shown to the user is as illustrated in FIG. 3B. In the example shown, the user has dragged and dropped both the dots and labels of the dosimeter sensors (e.g., A1, A2 etc.) so that the dots are located at the required sites on the images and the identification labels are conveniently placed nearby. A description of each site, e.g., "rear of neck", is optionally recorded in a database.

Having completed this task of assigning sensor icons to desired locations, the user may print out the diagram or photo of the patient with the sensor locations so that the medical personnel may then use the print as a guide when placing the dosimeter sensors in the desired locations on the patient.

Following irradiation, the dose information from the dosimeter sensors is read into the computer by operating the dosimetry system connected as in FIG. 1. (The dosimeters may be removed from the patient for this part of the procedure).

Figure 4:
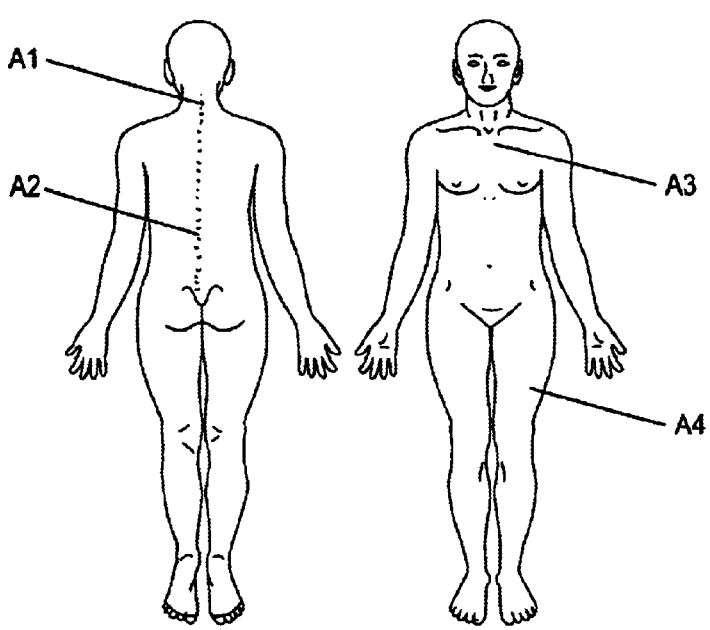
FIG. 4 illustrates a report provided by the system.

The dose measurements are stored in the computer and displayed on a final report, along with the patient and treatment information. FIG. 4 shows the format of the final report with the two representations of the patient's body and the sensor position information, as well as the actual dose measurements, the desired or target doses and the deviation information.

Figure 5:
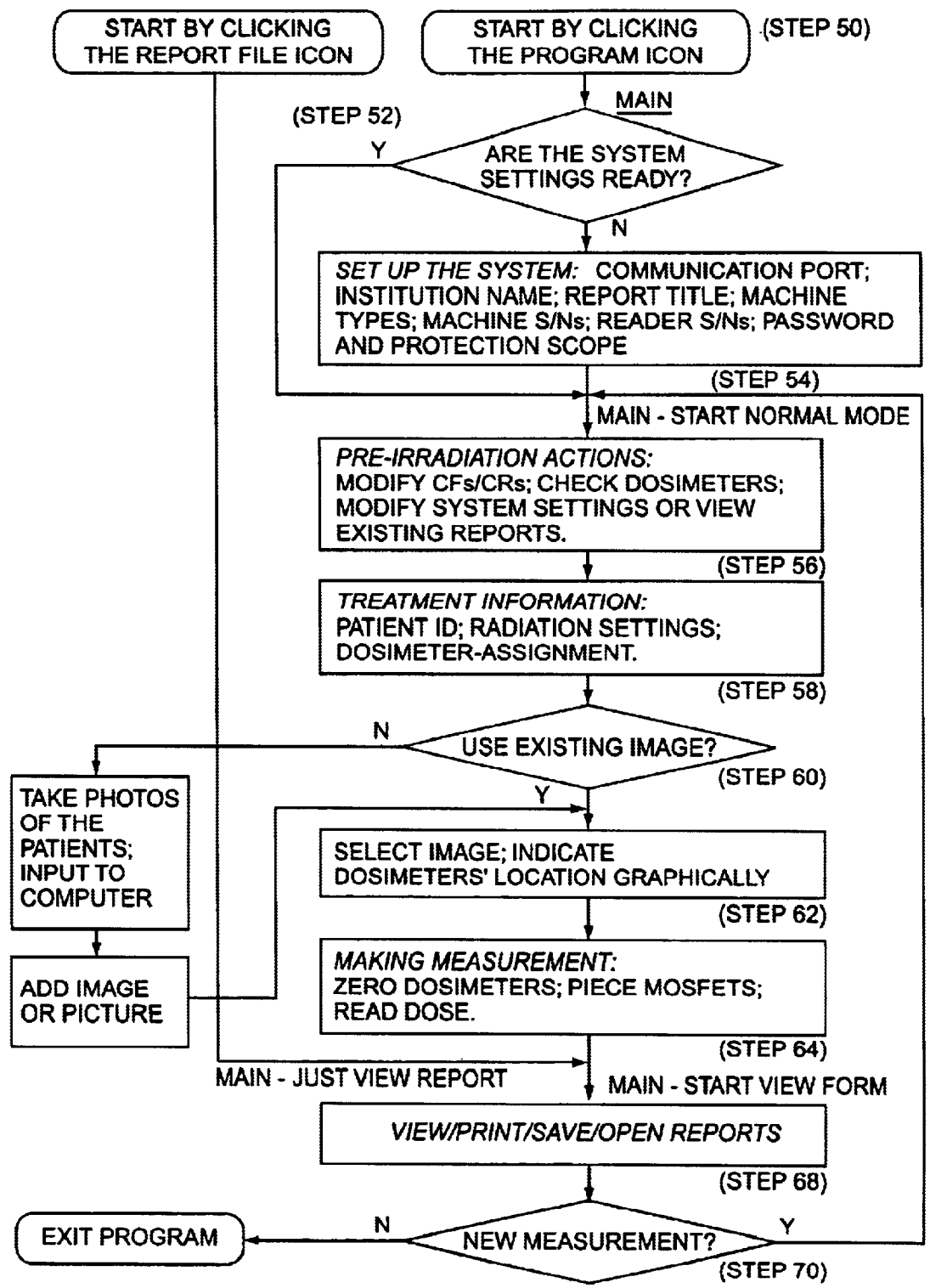
FIG. 5 is a flowchart depicting operation of the system.

The software used by the system may be developed using Visual Basic™ or any other software program suitably configured, to carry out the above process. The software program catalogs its functions into the following sections:

(i) System setup
(ii) Pre-irradiation
(iii) Treatment Information
(iv) Measuring Dose
(v) Viewing & Printing reports FIG. 5 shows a flow chart of the system software program. The main tasks the software needs to perform include: i) recording information sent by the Reader ii) organizing this information on the computer screen iii) recording treatment information, indicating dosimeters' position and iv) printing out measurement reports.

Figure 6A:
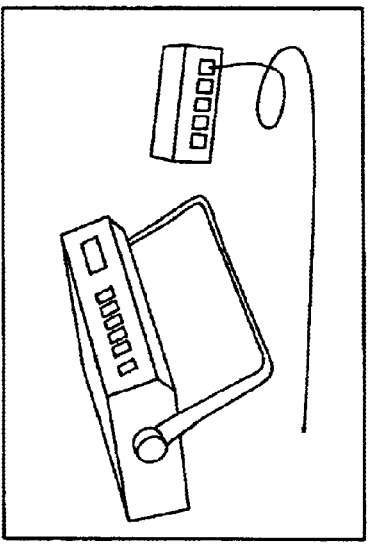
Figure 6D:
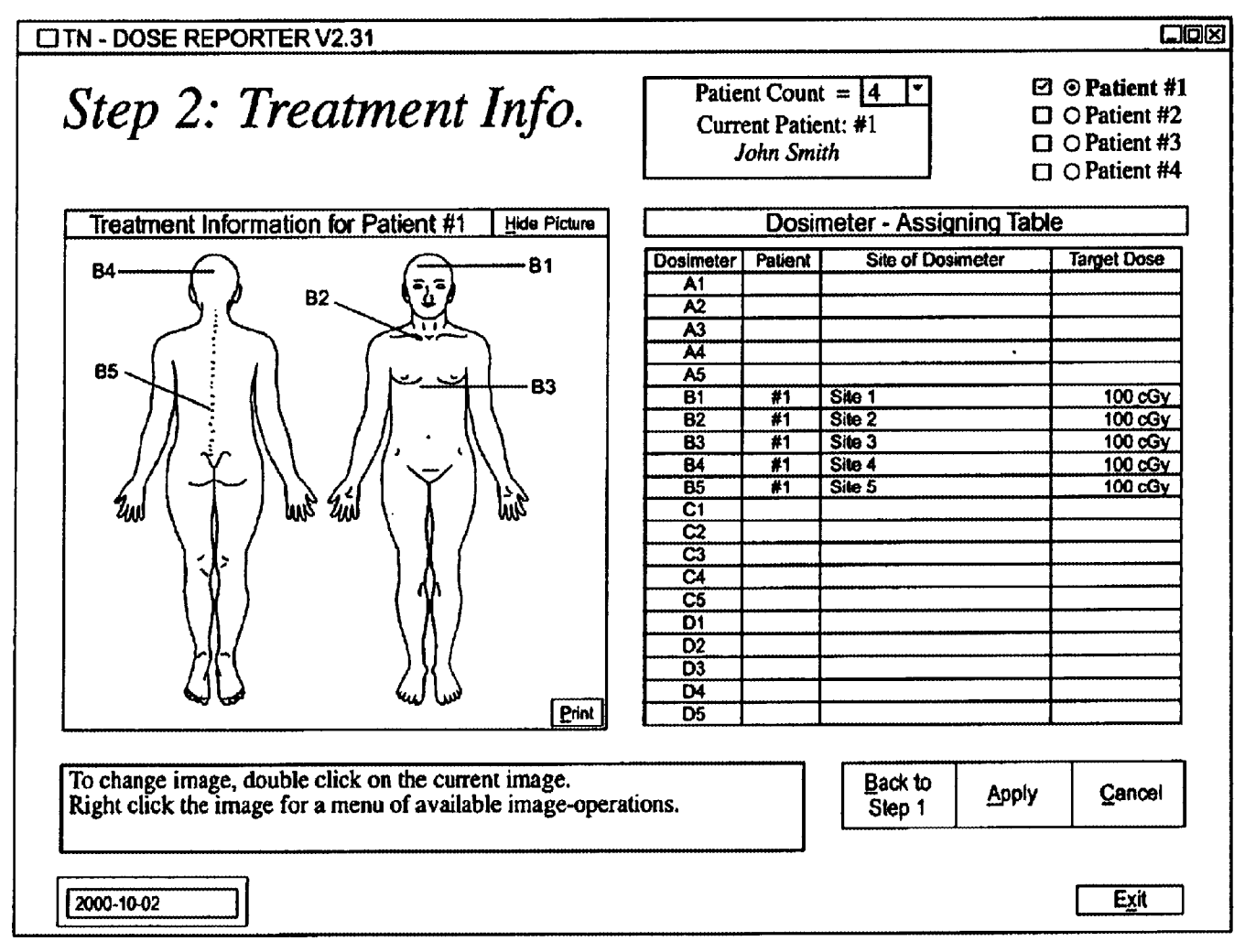

To start with, the user has the option of deciding if he wants to just view a report that is already existing (by clicking on the 'Report File' icon on screen) or to run the program for new readings. In the first instance, the user may view only the existing reports. In the latter case, the program is started by clicking the "Program" icon on the computer screen (step 50). A Start I Program menu is displayed on the screen. The program then checks if the system is set up (step 52) by checking all the initial set up parameters, e.g., if an appropriate port has been selected, if the password is correct etc. If the system is not set up, the user is prompted to click on the "TN-Dose Reporter 2.31" entry of the computer's "Start I Programs" menu to run the setup program and the "Setting Up the System" panel (FIG. 6A) is displayed on the computer screen (step 54). At this stage the user is prompted to input data like a password, Institution's name, the patient's name, selection of the communication port etc. Once the user appropriately inputs all the values required to set up the system, the program moves to the next step of Pre-Irradiation (step 56). The Pre-Irradiation display is shown on the monitor and in this step the user may modify calibration parameters, modify system settings etc (FIG. 6B) by entering desired data into the computer to be displayed on the screen. Once this step is completed the program moves to the step of Treatment Information (step 58). This can be carried out without picture (FIG. 6C) or with picture (FIG. 6D). A table is shown where the user may type in the appropriate information e.g., Patient-ID, Radiation setting and Dosimeter-Assignments. In the previous case the user may describe the dosimeter sensors' locations with words (e.g., 'chest', 'stomach' etc.) and type words in the corresponding cells of the dosimeter Assigning table (FIG. 6C). To do the latter, the user may click upon the "Show Picture" icon whereupon an image representing a human body will be displayed on the screen.

The user is prompted with an option to use the same image displayed on screen or select another image stored in the memory of the computer (step 60). If the user decides to select another image, the computer then instructs the user to assign dosimeter sensors to various parts of the anatomy and the user has to indicate the sensors locations on the newly selected image (step 62). There is also an option of taking an actual photograph of the patient using a digital camera and using that image on the screen instead of using previously stored images. The photograph thus taken may be displayed on screen by the program to be selected by the user.

The selected image is now provided in an on-screen picture box which accommodates the image as background and some labels, red dots and lines for linking a label with a dot, as foreground (FIG. 6D). Each label and dot may be "dragged and dropped" to appropriate positions on the image representing the human body to indicate the dosimeters' locations graphically. In the table provided on the screen, corresponding to each label or identifier representing a dosimeter sensor, a target dose of radiation may be entered.

Once labelling of the irradiation locations on the image corresponding to the patients body is successfully completed, the program performs the step of Making Measurement (step 64) and the next screen titled Making Measurement appears. The screen now displays a table where all the labels or identifiers representing the dosimeter sensors are shown, Dose data from the actual sensors placed on the patient's body is read by the reader 14 and is inputted to the computer and the data read is placed in the corresponding row in the table next to the identifiers which also represent the same dosimeter sensors identifiers marked on the image (FIG. 6E).

In the next step, the program extracts information and creates a report. The user is prompted for viewing/printing and saving the final reports. Once this option is selected, the dose measurements are stored in the computer and displayed on a final report (FIG. 6F) along with the patient and treatment information (step 68).

Next in a display the program asks the user if another measurement needs to be performed (step 70). If the answer is "No" the program exits. If the answer is "Yes", i.e., if the user decides to perform another measurement, the program goes back to step 54 and starts the Pre-Irradiation procedure again.

The software is generally composed of a) Visual Components, b) Main Module, c) Supporting Modules.

a) Visual components include the functional display panels and some supporting windows.

b) Main Module provides the entry point to run the software and is named as Lib_main. When the program starts to run, the main( ) subroutine in this module is called first followed by the other subroutines, e.g., main_tryPort( ), main_tryScreen( ) etc.

c) Supporting Modules consists of subroutines for performing various functions including:

Lib_Step0: stores the subroutines needed for the panel "Setting up the system"

Lib_Step1: provides subroutines needed for the panel "Pre-Irradiation"

Lib_Step2: consists of subroutines needed for the panel "Treatment Information"

Lib_Step3: stores the subroutines needed for the panel "Measuring Dose"

Lib_Step4: provides subroutines needed for the panel "Viewing/Printing Reports"

Lib_MyTypes: for defining some custom data types

Globals: for defining global variables

Lib_util: consists of general purpose service subroutines

Lib_comm: stores subroutines for communication with the Reader and subroutines for message analysis.

The following is a detail description of the steps the software carries out in order to proceed from System Setup to Viewing/Printing Reports.

1. System Setup

Prior to use, the system is set up by selecting the communication port of the computer to be used for reading the data from the reader, setting up the title of the measurement reports, setting or changing the password and determining its protection scope, inputting the lists of radiation machines and TN-RD-50 Readers. The user clicks on the "TN-Dose Reporter 2.31" entry of the computer's "Start I Programs" menu to run the program. The "Set Up the System" panel is shown (FIG. 6A) and the user is required to input some information or make some decisions, which include:

(1) Choosing a serial port to communicate with the TN-RD-50 Reader.

(2) Inputting the Institution Name and the Report Title. They will be printed on the measurement reports. The default Report Title is "DOSIMETRY REPORT".

(3) Building up the list of radiation machines types.

(4) Building up the list of radiation machines' S/N.

(5) Building up the list of TN-RD-50 Readers' S/N.

(6) Setting or changing the user's password and determining the password-protection's scope.

Once the system is set up, the "Set Up The System" panel will not be shown when the program is run later. To view or change system settings, the user can select the action of "Modify System Settings" from panel.

When the program is started, it checks the computer's hardware resources and lists all available serial ports in the pull-down list. If there is no port available (for example, in case all ports being used by other applications), the program will give out a message and automatically show the panel of "Viewing/Printing Reports".

After setup, a new folder (for example: "c:\TN-Dosimetry") is established in the computer. This folder holds a file for history of messages (e.g. "MessageHistory.txt") and two sub folders ("Libs" and "Reports"). These folders may not be renamed.

2. Pre-Irradiation

Once the set up process is completed, the computer will display one or more representations of the body to be irradiated and points or icons representing a plurality of dosimeter sensors in the panel of "Pre-irradiation" (FIG. 6B). In this step, the user can modify Calibration Factors (CFs) and Correction Factors (CRs), check dosimeter sensors, modify system settings, or view existing reports.

The Reader can be set to read in radiation units (cGy or R) using Calibration Factors determined by the user for each dosimeter. The Reader can also be set to read the MOSFET voltage in mV. In order to give the user more flexibility, this Dose Reporter program allows the user to store the CFs in the program when the mV mode is used. The program also enables the user to specify Correction Factors (CRs) to be used in the dose calculation.

If the Reader is set to output radiation units (cGy or R), then the CFs and CRs in the program are inoperable. If the user sets the output of the Reader to mV, then CFs and CRs must be set, because they will be used to calculate the doses according to the formula "Dose=CR*(Voltage/CF)". The user can get a hard copy of CFs and CRs by clicking the "Print" button.

[Note: An example of the use of a CR would be if the user wanted to determine Dmas but was measuring doses with less than full build-up.]

The allowed CF range is 0.1 mV/cGy to 99.99 mV/cGy. If the user enters a too large or too small value, it will be trimmed into this range. The allowed CR range is 0.100 to 9.000. If the user enters a value beyond this range, it will be trimmed into this range.

Figure 7A:
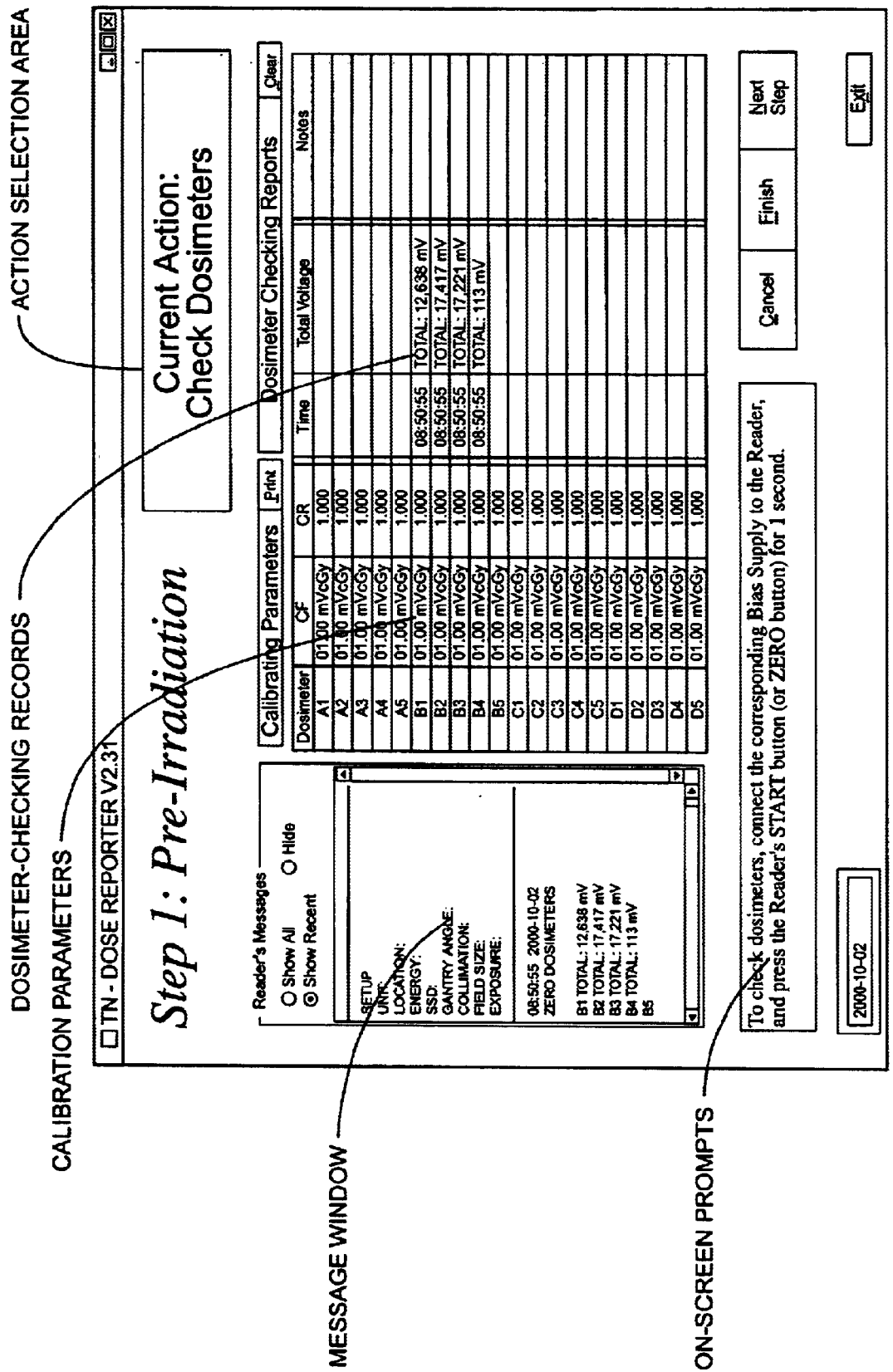
Figure 7C:

When the user has finished modifying CFs or CRs, the user can set them as defaults. Otherwise, the default CF and CR is 1.00 mV/cGy and 1.000 respectively. If the user does not like other users changing CFs or CRs (or both), the user can set up a password (in "Setting Up the System" Panel) and put CFs or CRs (or both) into the protection scope, then restart this program. A realistic example of this panel is shown in FIGS. 7B and 7C.

A Message Window is used to display the messages from the TN-RD-50 Reader. The user can view all messages (in the current measurement procedure) or just view recent messages. Every message displayed here is also saved into a file "c:\TN-Dosimetry\MessageHistory.txt" simultaneously.

3. Treatment Information

In this step, the user may adjust the display to position the sensor artefacts (points or icons) at preselected locations on, in or near the body at which radiation doses are to be measured by dragging the artefacts to various locations of the picture representing a human body on the screen (FIG. 6D). Optionally, this can be done without the image as well (FIG. 6C).

The user determines the number of patients in the current treatment, and, for each patient, selects the position on the screen to type in the appropriate information e.g. Patient's ID, Treatment Plan Reference and Radiation Settings.

There is an on-screen picture-box (See FIG. 2) which accommodates an image as background and some labels, lines and red dots as foreground. The user can select the background image from the software's built-in images, or use any image that has been stored in the computer's hard disk in BITMAP, JPEG or GIF format. For every assigned dosimeter sensor, the picture-box shows on the foreground a label, a red dot, and a line to link the label and dot. Every label and dot can be dragged to appropriate positions to indicate the dosimeters' sites graphically. Thus the user assigns dosimeter sensors to various locations on a patient's body through an on-screen table, and types in words to describe the locations and target doses of each dosimeter sensor.

FIG. 2 is an example of a picture that appears on the screen to let the user input the Patient Information, Treatment Plan Reference, and Radiation Settings (the user can set them by importing treatment information from an existing measurement report by clicking "Import Existing Treatment Info"). The user also needs to assign dosimeter sensors to the patient(s).

When the user assigns dosimeters to the current patient, the corresponding Site Pointer and Dosimeter Label will appear on the image area. To indicate the dosimeter sensor's site, the user may simply drag the Site Pointer and Dosimeter Label to the appropriate place on the image. (The user can drag the Pointer and Label to the same place, and the pointer will disappear.)

The user can describe the dosimeter sensors' locations with words or with pictures. To do the former, the user may type words in the corresponding cells of the dosimeter-Assigning Table (FIG. 6C). To do the latter, the user may click "Show Picture", whereupon a human body image will be displayed on screen, as FIG. 6D.

The software uses a table to store treatment information in this step. For every patient, the software creates an instance of this table that accommodates fields to keep Patient's ID, Treatment Plan Reference, Radiation Settings, Dosimeters' Positions and Target Doses. It also includes a field to keep a reference to the selected background image, and some fields to keep the relative coordination of every foreground label, dot and line.

Clicking the "Print" button on the picture's bottom-right corner can print out the picture. (If that button is not enabled, the user may click the "Apply" button.)

The user can change the human body image. For example, 5 optional images, called "Standard Images", are generally provided. They are

0, Unisex Body

1, Female Chest

2, Male Head

3, Female Head

4, Female Body

Besides the standard images, the user can use their own images, conveniently called "Custom Images", such as those from a digital camera photo or a scanned photo. Any BITMAP (*.bmp), JPEG (*.jpg) and GIF (*.gif) images can be used as a custom image. If the image to be used has been stored in another format, some tools (such as Paint or PhotoShop) may be used to open them and save them in BITMAP or JPEG format. There is no special requirement on the images' size.

Figure 7D:
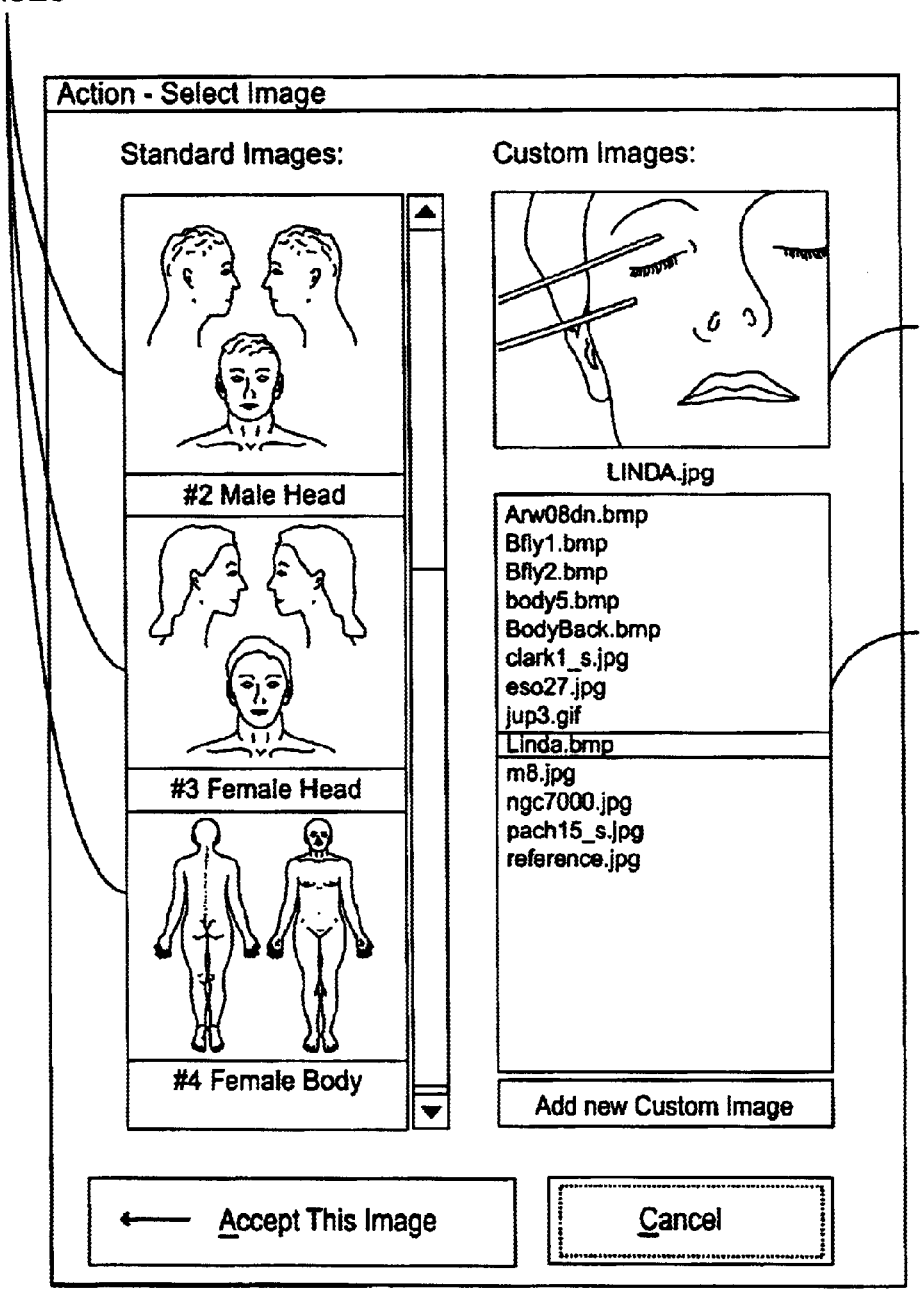

To change the image, the current image is double-clicked, or right-clicked to pop up a menu and in the menu "change image" in the menu is selected. An image-selection window, as in FIG. 7D, will be displayed on screen.

To select a standard image, its preview window is clicked. To select a custom image, the user should click on the corresponding item in the library of custom images to preview it, then, click on the preview window.

When the program is run for the first time, the library of custom images is empty. To populate it, the user may click the "Add new Custom Image" button, then select an image file from the open-file dialog box. That image will be copied to the library and can be used as a custom image by the program.

4. Measuring Dose

This step involves irradiating the body and obtaining data of radiation measured at each of the sensors. Dose data from the patient's body is read by the reader 14 through preassigned sensors (marked as e.g., A1, A2, A3 and A4) connected to the reader. Output from the Reader 14 is transmitted through a cable connected to the computer (by an RS-232 cable for example) and placed in the corresponding row in the table of recorded data on the screen. The user can activate the "Recording" procedure to allow the input data to overwrite the existing data, or freeze this procedure to prevent the recorded from being changed.

The panel of this step is shown in FIG. 6E. In this step, the user is required to perform 3 actions;

(1) Zero MOSFETS: press the Reader's START (or ZERO) button for 1 second to initiate the procedure.

(2) Place MOSFETS ON PATIENT(s) body. (To do it correctly, it is suggested that the user print out the dosimeter-site diagram as a reference.)

(3) Read MOSFETs: click the "Record" button on the screen, then follow the prompt.

In the measurement procedure, if "N/A" appears in the "Voltage" column, it means that the voltage is Not Available since the Reader has been set up to output doses in the radiation units cGy or R. Voltages are only shown in this column when the user is using the Reader in the "mV" mode and applying Calibration Factors (CFs) and/or Correction Factors (CRs) to translate m/v to radiation units. A realistic example of actual measurement is shown in FIG. 7E.

5. Viewing/Printing Reports

This step involves displaying and printing the data for each sensor in the same display as the one or more representations of the body with the sensor points or icons at said preselected positions. The software extracts the information, that is necessary to create a measurement report, from the inputted data in step 58 and recorded data in step 64. This information is stored into a special array. Then, from this array, a report summary is composed and the corresponding image (see FIG. 4) is drawn. If the user needs to save this report, the software will save all fields of this array to the hard disk of computer 18 (next time, they can be read into the array if needed). The data in this array is also used to print out the report. It may also be saved to a floppy disk or other removable storage medium or transmitted via a network or modem connection.

Figure 6F:
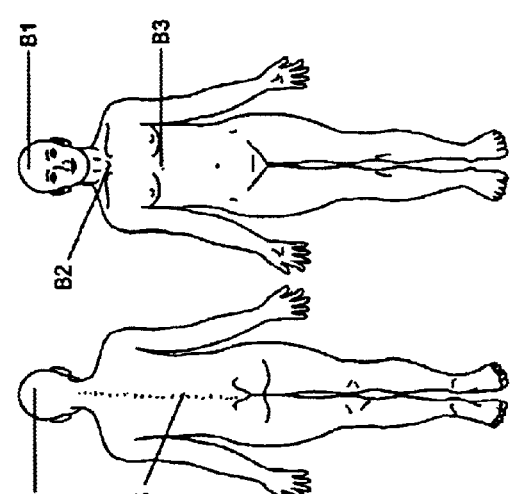

In this last step, the user can review the information in the report summary before printing and saving (FIG. 6F). All report files have a filename with extension ".dsrpt". The default file name may be "Patient First Name+Patient Last Name+Date+.dsrpt". For example, if John Smith was treated on May 10, 2000, then the default file name would be JohnSmith_2000May10.dsrpt The default folder for saving reports is "c:\TN-Dosimetry\Reports", but the user can save the reports in any folder.

When the user wants to print out the reports, there are two styles available. Style #1 accommodates a picture to indicate dosimeters' sites graphically. Style #2 doesn't print out the picture, but uses a table to provide more information about the treatment. In this step, the user can also type in comments.

It has been stated that an existing custom-image may be used to indicate dosimeters' locations, But, in fact, that image need not have to exist before the user runs the program. The user can use the REAL photos of the patient(s) in current treatment using a digital camera.

It should be appreciated that the software enabling implementation of the invention could be used with various kinds of hardware. Hence, the invention also embraces software perse, conveniently carried by a suitable storage medium, for operating a dosimetry system as described hereinbefore.

What is claimed is:

1. A method of determining locations of radiation sensors in, on or adjacent a body during subsequent irradiation thereof by a radiation therapy system, comprising the steps of:

(i) displaying on a display device, simultaneously, a representation of at least a portion of the body to be irradiated, and a plurality of graphics artefacts each representing a respective one of a plurality of radiation sensors to be positioned in, on or adjacent said body during subsequent irradiation of the body, each graphics artefact comprising a sensor icon and a sensor identifier;

(ii) controlling the display means to relocate, selectively, some or all of the sensor icons of the graphics artefacts at respective positions on or adjacent said representation, said positions corresponding to positions on, in or adjacent said body at which the radiation sensors represented by the selected sensor icons are to be positioned during subsequent irradiation of the body, and (iii) outputting to one or both of storage means and recording means a record of the displayed representation and graphics artefacts with the sensor icons in their relocated positions.

2. A method according to claim 1, wherein each of the sensor icons comprises a graphical point connected to the respective one of the plurality of identifiers by a line, and the step of adjusting positions of the icons comprises the step of adjusting either or both of the point and the identifier relative to each other and the representation of the body.

3. A method according to claim 1, further comprising the step of printing the representations of the body and the sensor icons placed at desired locations in relation to the representation of the body.

4. A method according to claim 1, wherein the step of displaying said representation and said graphics artefacts further comprises the step of displaying, also simultaneously, a plurality of desired radiation doses each associated with a respective one of the sensor identifiers and representing a level of radiation to be measured by the corresponding sensor during said subsequent irradiation of the body; and wherein said outputted displayed image record shows said desired radiation doses.

5. A method according to claim 4, further comprising the step of printing out the representations of the body and the sensor icons placed at desired positions in relation to the representation of the body with corresponding measured dose data associated with the sensor icons.

6. A method according to claim 5, wherein the measured data is displayed in tabular form.

7. A method according to claim 4, further comprising the steps of recording actual doses measured by said plurality of sensors during said subsequent irradiation of said body, and displaying a second display showing the representation, the graphics sensor icons in their relocated positions, the desired radiation doses, and the recorded actual doses, each desired radiation dose and corresponding recorded actual dose being associated in the display with the corresponding one of the sensor identifiers.

8. A method according to claim 7, wherein the sensor identifiers desired dose values and the corresponding measured dose data are displayed in tabular form.

9. A method according to claim 7, wherein the display means is controlled by a computer system coupled to a plurality of said radiation sensors by sensor recording means.

10. A dosimetry system comprising:
   (i) display means;
   (ii) display control means for controlling the display means to provide, simultaneously, a display image comprising a representation of at least a portion of a body to be irradiated and a plurality of graphics artefacts each comprising a sensor icon representing a respective one of a plurality of radiation sensors to be positioned in, on or adjacent the body during subsequent irradiation of the body, and a corresponding identifier;
   (iii) user-operable means for controlling the display control means to relocate, selectively, some or all of the sensor icons at respective positions on or adjacent said body image, said positions corresponding to positions on, in or adjacent said body at which the sensors themselves are to be positioned during subsequent irradiation of the body, and outputting to one or both of storage means and recording means a record of the displayed image showing the body image and graphics anefacts with the sensor portions positioned as relocated.

11. A dosimetry system according to claim 10, wherein said display control means is configured to display in said display image a plurality of desired dose values to be measured by the corresponding sensor during said subsequent irradiation of the body, each desired dose value being associated in the display with a respective one of the sensor identifiers, said user-operable means further comprising means for said user to input said desired dose values.

12. A dosimetry system according to claim 11, wherein the display control means is configured to control the display system to display the sensor identifiers, desired dose values and corresponding measured actual doses in tabular form.

13. A dosimetry system according to claim 11, wherein the display control means is configured to cause the display means to display as said representation one or more drawings of said at least a portion of the body.

14. A dosimetry system according to claim 11, wherein the display control means is configured to cause the display means to display as said representation one or more photographs of said at least a portion of the body.

15. A dosimetry system according to claim 11, wherein each of the sensor icons comprises a graphical point and the associated one of the plurality of identifiers is connected to the graphical point by a line, and the display control means has means for adjusting positions of either or both of the point the identifier relative to each other and the representation of the body.

16. A dosimetry system according to claim 15, wherein the display control means is configured to print the representations of the body and the sensor icons following the adjustment of the positions of either or both of the point and the identifier.

17. A dosimetry system according to claim 11, further comprising sensor reader means for coupling the display control means to a plurality of said sensors and recording actual doses measured by said plurality of sensors during said subsequent irradiation of said body, and wherein the display control means is configured to cause the display means to display the desired dose values actual measured doses, each associated with the corresponding one of said sensor identifiers.

18. A dosimetry system according to claim 17, wherein the display control means is configured to cause the display means to display as said representation one or more drawings of said at least a portion of the body.

19. A dosimetry system according to claim 17, wherein the display control means is configured to cause the display means to display as said representation one or more photographs of said at least a portion of the body.

20. A dosimetry system according to claim 17, wherein the display control means comprises a personal computer.

21. A storage medium carrying software for controlling a dosimetry apparatus to perform a method of determining locations of sensors in, on or adjacent a body prior to radiation by a radiation therapy system, the method comprising the steps of:
   (i) displaying a display image comprising a representation of at least a portion of the body to be irradiated, and a plurality of graphics artefacts each representing a respective one of a plurality of radiation sensors to be positioned in, on or adjacent said body during subsequent irradiation of the body, each graphics artefact comprising a sensor icon and a sensor identifier;
   (ii) adjusting the display image to relocate, selectively, some or all of the sensor icons at respective positions on or adjacent said representations, said positions corresponding to positions on, in or adjacent said body at which the actual radiation sensors are to be positioned during subsequent irradiation of the body, and
   (iii) recording the display image with the sensor icons positioned as relocated.

* * * * *